United States Patent
Wegman

[11] Patent Number: 6,086,872
[45] Date of Patent: *Jul. 11, 2000

[54] AMELIORATION OF DUPUYTREN'S DISEASE

[75] Inventor: Thomas L. Wegman, North Merrick, N.Y.

[73] Assignee: Advance BioFactures of Curacao, NV, Curacao, Netherlands

[*] Notice: This patent is subject to a terminal disclaimer.

[21] Appl. No.: 08/826,015

[22] Filed: Mar. 27, 1997

[51] Int. Cl.[7] ............ A61K 38/43; A61K 38/46; A61K 38/48; C12N 11/02
[52] U.S. Cl. ............ 424/94.67; 424/94.1; 424/94.63; 435/177
[58] Field of Search .................. 424/94.1, 94.63, 424/94.67; 435/177

[56] References Cited

U.S. PATENT DOCUMENTS

| | | | |
|---|---|---|---|
| 4,338,300 | 7/1982 | Gelbard | 424/94 |
| 5,589,171 | 12/1996 | Wegman | 424/94.67 |

FOREIGN PATENT DOCUMENTS

| | | |
|---|---|---|
| 543521 | 5/1993 | European Pat. Off. . |

OTHER PUBLICATIONS

J. of Hand Surgery (1996) 21/3 490–495.

*Primary Examiner*—Michael G. Wityshyn
*Assistant Examiner*—Deborah K. Ware
*Attorney, Agent, or Firm*—John D. Upham; Roland Plottel

[57] ABSTRACT

The cords of Dupuytren's disease are injected with collagenase, the hand is immediately immobilized and maintained immobile for several hours. The cord becomes relaxed or ruptured, relieving the hand contracture of the disease.

20 Claims, No Drawings

AMELIORATION OF DUPUYTREN'S DISEASE

BACKGROUND

Dupuytren's disease (Dupuytren's contracture) of the hand occurs mainly, though not exclusively, in men. It is found more frequently in middle aged and elderly persons, in those of Northern European ancestry, and in those with certain chronic illnesses, e.g. diabetes, alcoholism and smoking. The cause is not known.

The disease is characterized by thickening and contracture of the fascia (connective tissue) of the palm, usually progressing to flexion deformities and involvement of one or more fingers. This results from formation of longitudinal cords of indurated fibrous tissue in the palm and extending into the finger. A similar lesion sometimes occurs in the foot. No effective palliative treatment has been found; severe cases are treated by surgery (fasciotomy or fasciectomy).

Currently, the most commonly performed therapy for involutional and for residual stages of Dupuytren's disease is surgical fasciectomy (i.e., removal). Several authors have proposed alternate, nonsurgical modes of therapy involving chemical or enzymatic fasciotomy. Investigators have used Vitamin E, dimethysulfoxide (DMSO), tocopherol, X-rays and physical therapy with no resultant therapeutic benefit. Additionally, case reports describing the use of allopurinol and methylhydrazine and steroids have shown some immediate but no long term benefit. Hueston reported on the use of a mixture of trypsin, hyaluronidase, and lidocaine injected into Dupuytren's nodules and cords in 12 patients with subsequent rupture of the diseased fascia upon forcible finger extension but no long term benefits.

E. Ippolito et al. (Experimental Study On the Use of Collagenase in Localized Connective Tissue Fibrosis, Ital. J. Orthop., Traumatol., Vol. 1/2, 279–290 [1975]) used rabbit tendons as a model for Dupuytren's cords. In vivo tests infiltrated the Achilles tendon of rabbits with 1 cc of a solution of Worthington collagenase. The solutions contained, respectively, 40, 80 and 160 Worthington units of the enzyme per cc. (One Worthington unit is approximately equal to two ABC units.) At sacrifice after 24 hours, the tendon infiltrated with 40 Worthington units showed no signs of digestion, while the tendon infiltrated with 160 Worthington units showed massive digestion.

Wegman, Thomas L., U.S. Pat. No. 5,589,171, Dec. 31, 1996, teaches treatment of Dupuytren's disease by injecting collagenase into the fibrous cord. Data are presented in which excised cords are treated in vitro. In one experiment, 3,600 ABC units of collagenase in 0.5 ml diluent was injected into each of ten cords, which were then incubated for 24 hours. The mean tensile modulus was reduced and collagen bundle disruption was observed. In another in vitro experiment, excised cords were cut into pieces and incubated 48 hours with different concentrations of collagenase in diluent ranging from 225 to 900 ABC units per ml. Examination of sections of the treated cords revealed increasing disruption of collagen. It was concluded that 450 ABC units per ml was a suitable concentration.

BRIEF SUMMARY OF THE INVENTION

Successful relief from the hand contracture of Dupuytren's disease is obtained by injecting an effective amount and concentration of collagenase into the fibrous Dupuytren's cord, immobilizing the hand immediately after injection, and maintaining it immobile for several hours. Best results are obtained when the patient is in the residual stage of the disease.

DETAILED DESCRIPTION

Collagenase is an enzyme that has the specific ability to digest collagen. It is derived commercially from fermentation by *Clostridium histolyticum,* and is purified by a chromatographic technique.

The potency assay of collagenase is based on the digestion of undenatured collagen (from bovine tendon) at pH 7.2 and 37 degrees C for 20–24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

Sterilized lyophilized collagenase powder is available having a minimum assay of 50 ABC units per mg. The assay may range considerably above that from batch to batch, but is taken into account in determining the weight of powder to use with a pharmaceutically acceptable carrier, e.g. normal saline, in preparing a desired concentration for treatment.

The collagenase is applied in a liquid carrier that is pharmaceutically acceptable, including inertness towards the collagenase. Examples are normal saline, aqueous NaCl/CaCl2 buffer, aqueous dextran solution, aqueous hetastarch solution.

In accordance with the invention, collagenase in a liquid carrier is injected into a fibrous Dupuytren's cord, and immediately thereafter the hand is immobilized, as by wrapping with sufficient gauze bandage and in such a way as to form a bulky dressing. The hand, and especially the affected finger, is thus prevented from substantial movement. The immobilization is continued for several hours, e.g., 4 to 10 hours. It is believed that this may minimize expression of the collagenase solution out of the cord, and allows sufficient but not excessive time for action of the collagenase on the cord, resulting in good clinical outcomes. Typically, if the injection takes place during the early part of the afternoon, the dressing is removed at bedtime.

The amount and concentration of collagenase used are effective to soften and relax or rupture the cord. The tension exerted by the cord that has been holding the finger bent being thus relieved, the finger soon straightens, usually completely.

It is preferred to inject sufficient collagenase solution into the Dupuytren's cord to provide a total amount of at least 8,000 ABC units, and preferably an amount within the range of 8,000 to about 15,000 ABC units. The preferred concentration of collagenase in carrier is within the range of about 15,000 to about 75,000 ABC units per ml of carrier. Suitable combinations, for example, are at least 8,000 ABC units in a concentration of at least 30,000 units/ml; at least 10,000 units in a concentration of at least 40,000 units/ml. In general, the lower the amount of collagenase, the greater should be the concentration. Thus, if in a particular situation it should be desired to use 5,000 ABC units, a concentration of 20,000 to 50,000 units/ml would be desirable.

The total volume of liquid injected preferably does not exceed about 0.5 ml. A smaller volume down to about 0.25 ml to about 0.1 ml is usually more preferred.

In important aspects of the invention, the total dosage per cord is injected in multiple portions, preferably at least three, at different points in the cord but in close proximity to each other. These points are desirably a distance of about 2 mm apart, and usually are at or near the metacarpophalangeal joint and/or the proximal interphalangeal joint. The needle of the injection syringe should not be inserted at a right angle to the cord, but at acute angles. The objective of these procedures is to assure good distribution of the collagenase within a small volume of the cord.

In cases where results of a single treatment are considered inadequate, the same procedures, total amount of collagenase and concentration may be repeated at weekly intervals for one up to not over five times.

Dupuytren's disease is slowly progressive over the course of many years causing fixed flexion deformities in the metacarpophalangeal (MP) and proximal interphalangeal (PIP) joints of the fingers. The small and ring fingers are the most often affected. The disease progresses through three stages as delineated by Luck JV, J. Bone Joint Surg. 41A:635–664, 1959. The initial proliferative stage is characterized by nodule formation in the palmar fascia in which a cell known as the myofibroblast (Gabbiani G., Majno G. Am. J. Pathol. 66:131–138, 1972) appears and begins to proliferate. The involutional or mid disease stage is the focus of extreme myofibroblast proliferation and active type III collagen formation by these cells. In the last or residual phase the nodule disappears with the disappearance of the myofibroblast and only a dense fibrous type I collagen cord, histologically similar to a tendon, remains.

The best use of this invention is in the treatment of the residual (end) phase of Dupuytren's disease. The rationale for injecting cords instead of Dupuytren's nodules or the involutional (mid) stage is that cords contain a sparse population of fibroblasts, are relatively avascular and are predominantly composed of type I collagen but do not contain myofibroblasts as do nodules and mid-stage. There is no evidence to suggest that collagenase is cytotoxic to myofibroblasts. Therefore, injection of collagenase into nodules or the mid-stage, containing myofibroblasts, would most likely result in early recurrence or worsening of the hand contracture. This may be the reason that prior non-operative treatments have failed. This shortcoming can be overcome by injecting residual stage cords in accordance with the present invention.

EXPERIMENTAL

In all of the experimental work, Nucleolysin® from Advance Biofactures Corporation of Lynbrook, New York, was used. This is collagenase obtained by fermentation of *Clostridium histolyticum,* purified by chromatography, and lyopholized. It was diluted to desired concentration with an aqueous buffer of 0.2 mM calcium chloride and 0.9% sodium chloride.

Study A

In a controlled pilot experiment, 3,600 ABC units collagenase in 0.5 ml buffer was injected into ten Dupuytren's cords obtained from patients undergoing fasciectomy. As control, ten other cords handled at the same time in the same manner were injected with 0.5 ml buffer only. All were then incubated at 37 C for 24 hours. By stretching the treated cords in a Chatillon machine and measuring stress and strain, it was determined that the collagenase-injected cords underwent a 93% decrease in tensile modulus as compared with controls.

The investigators concluded that "a dose of 3,600 units was far in excess of that needed for cord rupture in Dupuytren's disease."

A controlled multiple dose in vitro study was then performed. Twenty cords were obtained from patients at surgery, and the specimens were randomly assigned to one of four groups: 150 ABC units, 300 ABC units, and 600 ABC units collagenase, and a control buffer group. Each group contained five cords. All the patients were men. The mean patient age for the 600 unit group was 62 years, for the 300 unit group 58, for the 150 unit group 67, and for the control group 58.

The cords were injected in the midsubtance with either buffer or 150, 300, or 600 ABC units collagenase, each injection being of 0.2 ml volume. They were then incubated at 37 C for 24 hours. Thereafter, each cord was stretched in a Chatillon machine until the cord broke.

It was found that a dose of 300 ABC units of collagenase was sufficient to cause cord rupture within the average maximum force limits of the finger extensors of the small, ring, and long and index fingers. Histologically, all samples obtained were in the residual disease stage and contained only type I collagen after Sirrius red stainings.

This Study A has been reported in The Journal of Hand Surgery, Vol. 21A, No. 3, May 1996, 490–495.

Study B

Subsequent to Study A, an in vivo series of tests was conducted on patients in the residual stage of Dupuytren's disease, by the same investigators. When 300 ABC units of collagenase in 0.1 ml of buffer diluent gave no effect, tests were made at doubling dosages, viz. 600, 1,200, 2,400, 4,800 and 9,600 ABC units, each dosage in 0.1 ml diluent, one patient for each dosage. A single injection at an angle of 90 degrees to the Dupuytren cord was made near the metacarpophalangeal joint (MP) of the hand. After waiting two hours, the patients were instructed to actively extend their finger in an attempt to rupture the cord.

No effect was seen in any of these patients.

Study C

A different approach was then adopted. The injection was made near the MP joint at three different places about 2 mm apart, the needle being at an oblique angle to the axis of the cord and inserted at different angles, the desired total dosage thus being delivered in multiple increments.

Prior to injection, the depth of the Dupuytren's cord in the hand was measured by ultrasound visualization using an Alkoa Model 210 manufactured by Corometrics. This enables the physician to avoid injection of the underlying flexor tendon.

The extent of flexion of the finger at the MP joint was measured in degrees by a digital goniometer.

The total dosage was 10,000 ABC units in 0.5 or 0.25 ml diluent.

Immediately after injection, the hand was wrapped in a bulky gauze dressing and immobilized for several hours. Typically the injection occurred at noon or shortly thereafter, and the bandage was removed at bedtime. The patients were encouraged not to try to extend or flex the fingers.

Using these procedures, excellent clinical results were obtained.

1. A 75 year old female had a 40 degree angle of flexion of her left ring finger. The Dupuytren's cord was injected, as described above, with 10,000 ABC units of collagenase in 0.5 ml of buffer solution. Significant swelling resulted, but it subsided by the following day. After one week, the flexion angle had decreased to 25 degrees. After two weeks, it was zero, i.e. normal, and remained so. After seven months, the cord could still be seen under the skin, but it was flatter and softer than it was pre-injection, and the formerly deformed finger was still straight.

The following three patients were injected with 10,000 ABC units collagenase in 0.25 ml buffer diluent.

2. The right small finger of a 64 year old male was bent 60 degrees, i.e. its angle of flexion measured 60 degrees. On follow-up the first day after injection, it was 45 degrees and at one week was zero.

3. A 64 year old male had a very thick Dupuytren's cord, extending from the palm into the left ring finger which had a flexion angle of 45 degrees. One day post-injection it was 30 degrees, and had decreased to zero (normal) by the fifth day.

4. A male 64 years old had a Dupuytren's contracture pulling his right small finger to a flexion of 60 degrees. Post-injection, it was 45 degrees after one day, 25 degrees after two days, and normal, i.e. zero degrees, after five days.

I claim:

1. A method of treating an individual suffering from Dupuytren's disease which comprises injecting collagenase into a fibrous Duputyren's cord in a hand of the individual suffering from the disease, immobilizing the hand immediately after injection, and maintaining the hand immobile for several hours, the amount and concentration of the collagenase being effective to relax or rupture the cord whereby the finger flexure caused by the cord is ameliorated.

2. A method according to claim 1 wherein a total amount of collagenase of at least 8,000 ABC units is injected in a pharmaceutically acceptable carrier in a concentration of at least about 30,000 ABC units per ml.

3. A method according to claim 2 wherein the total amount of collagenase is at least 10,000 ABC units and the concentration is at least about 40,000 ABC units per ml.

4. A method according to claim 1 wherein the collagenase is injected in a pharmaceutically acceptable carrier and the total volume of liquid injected does not exceed about 0.5 ml.

5. A method according to claim 4 wherein the total volume of liquid injected is in the range of 0.25 to 0.1 ml.

6. A method according to claim 1 wherein the injection is effected at multiple points in close proximity.

7. A method according to claim 6 wherein the injections are made at least three points in close proximity.

8. A method according to claim 1 wherein the individual is in the residual stage of Dupuytren's disease.

9. A method according to claim 1 wherein the hand is maintained immobile for a period of from 4 to 10 hours.

10. A method according to claim 1 wherein the injections are made at or near the metacarpophalangeal joint and/or the proximal interphalangeal joint.

11. A method according to claim 1 wherein the depth of the Dupuytren's cord in the hand is quantified by ultrasound scanning prior to injecting the collagenase.

12. A method according to claim 1 wherein the collagenase is in a pharmaceutically acceptable aqueous carrier.

13. A method of treating an individual suffering from Dupuytren's disease which comprises injecting into a fibrous Dupuytren's cord in a hand of the individual suffering from the disease an effective total amount of at least 8,000 ABC units of collagenase.

14. A method according to claim 13 wherein the individual is in the residual stage of Dupuytren's disease.

15. A method according to claim 13 wherein the total amount of collagenase is within a range of 8,000 to about 15,000 ABC units.

16. A method according to claim 13 wherein the collagenase is applied in a pharmaceutically acceptable carrier in a concentration of about 15,000 to about 75,000 ABC units collagenase per ml of carrier.

17. A method according to claim 13 wherein the collagenase is injected in a pharmaceutically acceptable carrier and the total volume of liquid injected does not exceed about 0.5 ml.

18. A method according to claim 17 wherein the total volume of liquid injected is in the range of about 0.25 to 0.1 ml.

19. A method according to claim 13 wherein the injections are made at acute angles to the cord.

20. A method according to claim 13 wherein the collagenase is in a pharmaceutically acceptable aqueous carrier.

* * * * *